United States Patent
McDonough et al.

(10) Patent No.: US 6,669,626 B1
(45) Date of Patent: Dec. 30, 2003

(54) HUMIDIFIER FOR A PATIENT SUPPORT APPARATUS

(75) Inventors: Robert M. McDonough, Hatfield, PA (US); Richard Hude, Fairless Hills, PA (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/913,949
(22) PCT Filed: Dec. 23, 1999
(86) PCT No.: PCT/US99/30953
§ 371 (c)(1), (2), (4) Date: Sep. 27, 2001
(87) PCT Pub. No.: WO01/47462
PCT Pub. Date: Jul. 5, 2001

(51) Int. Cl.⁷ .............................................. A61G 11/00
(52) U.S. Cl. ........................................................ 600/22
(58) Field of Search ..................................... 600/21–22

(56) References Cited

U.S. PATENT DOCUMENTS

| | | |
|---|---|---|
| 1,430,548 A | 10/1922 | Hogue |
| 1,749,969 A | 3/1930 | Brodin |
| 2,365,243 A | 12/1944 | Boren |
| 2,366,630 A | 1/1945 | Kreiselman |
| 2,454,657 A | 11/1948 | Kuzmin et al. |
| 2,633,842 A | 4/1953 | Higgs |
| 2,648,327 A | 8/1953 | Gibbon |
| 2,708,927 A | 5/1955 | Dixon et al. |
| 2,721,252 A | 10/1955 | Dorsak |
| 2,847,546 A | 8/1958 | Crowley et al. |
| 3,076,451 A | 2/1963 | Stoner |
| 3,084,492 A | 4/1963 | Dorsak et al. |
| 3,090,857 A | 5/1963 | Oberg |
| 3,158,150 A | 11/1964 | Croasdaile |
| 3,187,744 A | 6/1965 | Dorsak et al. |
| 3,219,795 A | 11/1965 | Wiseman |
| 3,282,266 A | 11/1966 | Walker, Jr. |
| 3,335,713 A | 8/1967 | Grosholz et al. |
| 3,464,388 A | 9/1969 | Stout |
| 3,511,162 A | 5/1970 | Truhan |
| 3,529,590 A | 9/1970 | Grosholz |
| 3,638,926 A | 2/1972 | Melville et al. |
| 3,782,362 A | 1/1974 | Puzio |
| 3,806,102 A | 4/1974 | Valenta et al. |
| 3,821,947 A | 7/1974 | Schossow |

(List continued on next page.)

FOREIGN PATENT DOCUMENTS

| | | |
|---|---|---|
| EP | 0449233 A1 | 2/1991 |
| EP | 0623746 A1 | 11/1994 |
| EP | 0687457 B1 | 5/2000 |
| GB | 2067077 A | 7/1981 |
| GB | 2175213 A | 11/1986 |
| JP | 122184/1974 | 11/1974 |
| NL | 2061704 | 12/1970 |

OTHER PUBLICATIONS

"Stabilet® From Hill–Rom®" Product Brochure, six pages, 1992.
"Infa–Care 2000", Infa–Care, Inc. Product Brochure, six pages, 1972.
"Stabilet CC™ From Hill–Rom®" Product Brochure, six pages, 1992.
"The Stabilet™ Freestanding Warmer and Clinical Bassinet From Hill–Rom®" Product Brochure, four pages, 1993.
"A Hill–Rom Solution", Stabilet 2000C, Stabilet CC, Stabilet Freestanding Infant Warmer Accessories Product Brochure, eight pages, 1995.

*Primary Examiner*—John P. Lacyk
(74) *Attorney, Agent, or Firm*—Barnes & Thornburg

(57) ABSTRACT

This invention is a humidifier for a patient support apparatus. The humidifier includes a vaporizer and a container. The container defines a reservoir. It is movable relative to the vaporizer between a first position operably coupled to the vaporizer and a second position spaced apart from the vaporizer.

23 Claims, 5 Drawing Sheets

U.S. PATENT DOCUMENTS

| | | |
|---|---|---|
| 3,854,452 A | 12/1974 | Bardet |
| 3,954,920 A | 5/1976 | Heath |
| 3,982,095 A | 9/1976 | Robinson |
| 3,987,133 A | 10/1976 | Andra |
| 3,990,441 A | 11/1976 | Hoyt et al. |
| 4,133,302 A | 1/1979 | McGrath et al. |
| 4,161,172 A | 7/1979 | Pickering |
| 4,284,878 A | 8/1981 | Bartels |
| 4,346,701 A | 8/1982 | Richards |
| 4,356,967 A | 11/1982 | Lunick |
| 4,361,137 A | 11/1982 | Grosholz |
| 4,500,480 A | 2/1985 | Cambio, Jr. |
| 4,529,867 A | 7/1985 | Velnosky et al. |
| 4,563,313 A | 1/1986 | Tsuaki |
| 4,572,427 A | 2/1986 | Selfridge et al. |
| 4,606,299 A | 8/1986 | Grumbach |
| 4,617,912 A | 10/1986 | Beer et al. |
| 4,652,408 A | 3/1987 | Montgomery |
| 4,701,415 A | 10/1987 | Dutton et al. |
| 4,750,474 A | 6/1988 | Dukhan et al. |
| 4,753,758 A | 6/1988 | Miller |
| 4,796,605 A | 1/1989 | Sasaki et al. |
| 4,846,783 A | 7/1989 | Koch et al. |
| 4,936,824 A | 6/1990 | Koch et al. |
| 5,162,038 A | 11/1992 | Wilker |
| 5,224,923 A | 7/1993 | Moffett et al. |
| 5,242,375 A | 9/1993 | McDonough |
| 5,330,415 A | 7/1994 | Storti et al. |
| 5,336,156 A | 8/1994 | Miller et al. |
| 5,453,077 A | 9/1995 | Donnelly et al. |
| 5,498,229 A | 3/1996 | Barsky et al. |
| 5,539,854 A | 7/1996 | Jones et al. |
| 5,616,115 A | 4/1997 | Gloyd et al. |
| 5,759,149 A | 6/1998 | Goldberg et al. |
| 5,792,041 A | 8/1998 | Kobayashi et al. |
| 5,797,833 A | 8/1998 | Kobayashi et al. |
| 5,878,190 A | 3/1999 | Gloyd et al. |
| 5,897,485 A | 4/1999 | Koch |
| 6,024,694 A | 2/2000 | Goldberg et al. |
| 6,031,968 A | 2/2000 | Holtmann |
| 6,090,036 A | 7/2000 | Kobayashi et al. |
| 6,256,454 B1 | 7/2001 | Dykes |

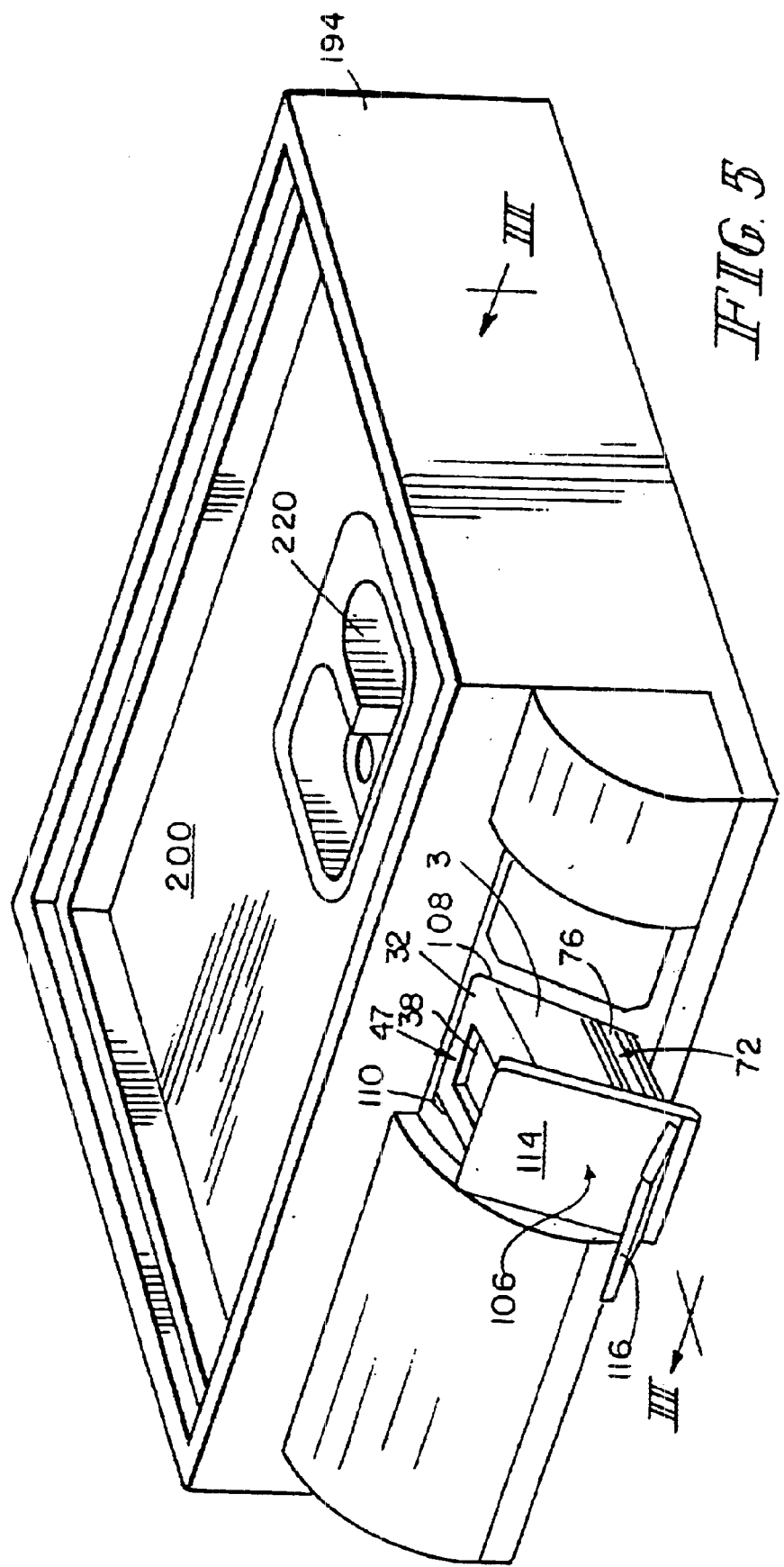

HUMIDIFIER FOR A PATIENT SUPPORT APPARATUS

CROSS-REFERENCES TO RELATED APPLICATIONS

This application is a U.S. national counterpart application of international application serial No. PCT/US99/30953 filed Dec. 23, 1999.

TECHNICAL FIELD

The present invention relates to a humidifier. More particularly, the present invention relates to a humidifier to be used in an infant care support apparatus.

BACKGROUND ART

Patient or infant care support apparatus provide controlled temperatures and humid environments for small or premature infants. A typical support apparatus provides a generally transparent enclosure within which heated and humidified air is circulated to minimize the heat loss of the infant. Such apparatus are provided with a large access door to allow for placement or removal of the infant. Supplemental access ways, such as hand ports or small entry doors, are also often provided to permit routine care of the infant while minimizing heat loss from the apparatus.

Typically, infant care support apparatus include built-in humidifiers through which filtered inlet air is passed. Other support apparatus may include external humidifiers which introduce filtered humidified air into the support apparatus. These humidifiers, however, are often configured or positioned such that refilling and cleaning their reservoirs can be difficult. It would be beneficial, therefore, to provide a humidifier that is movable with respect to the support apparatus and is both convenient to refill and to clean.

SUMMARY OF THE INVENTION

The present invention provides a humidifier for use in combination with a patient support apparatus. The humidifier comprises a vaporizer and a container. The container defines a reservoir and is movable relative to the vaporizer between a first position operably coupled to the vaporizer and a second position spaced apart from the vaporizer.

Another embodiment of the present invention provides an infant incubator comprising a tub and a humidifier. The tub carries a patient support surface. The humidifier comprises a vaporizer carried by the tub, and a container defining a reservoir. The container is movable relative to the vaporizer and relative to the tub between a first position received by the tub and operably coupled to the vaporizer, and a second position spaced apart from the vaporizer and spaced apart from the tub.

A further embodiment of the present invention provides an infant incubator also comprising a tub and a humidifier. In this embodiment, the tub carries a patient support surface and has a wall defining a perimeter of the incubator. The humidifier comprises a vaporizer and a container also carried by the tub. The container defines a reservoir and is formed to include an opening in fluid communication with the reservoir. The container is movable relative to the vaporizer and relative to the tub between a first position within the perimeter of the incubator and a partially spaced apart position providing access to the opening in the container, thereby providing access to the reservoir from outside of the perimeter defined by the tub.

In various embodiments of the present invention, the humidifier is made from a material that can withstand high temperature sterilization and is movable to a third position spaced apart from the patient support apparatus. In addition, the humidifier may include a container supported on a slide, a refill pan to refill the container while in the second position, a valve to provide fluid communication between the reservoir and the container, a manifold to engage the valve when the container is in the first position, a front panel to provide a grippable body to move the container between positions, a catch basin positioned to catch excess fluid, a latch to secure the container to the patient support apparatus, a spring to bias the valve member, and a seal movable between an open and closed position.

Additional features of the invention will become apparent to those skilled in the art upon consideration of the following detailed description exemplifying the best mode of carrying out the invention as presently perceived.

BRIEF DESCRIPTION OF THE DRAWINGS

The present invention will be described with reference to the attached drawings which are given as non-limiting examples only, in which:

FIG. 4 is a sectional view of a portion of the patient support apparatus of FIG. 5, taken along line II—II;

FIG. 5 is another perspective view of a portion of the patient support apparatus according to one embodiment of the present invention.

Corresponding reference characters indicate corresponding parts throughout the several views. The exemplification set out herein illustrates an embodiment of the invention, in one form, and such exemplification is not to be construed as limiting the scope of the invention in any manner.

DETAILED DESCRIPTION OF THE DRAWINGS

The patient support apparatus of the present invention may be constructed and operated in accordance with those apparatus shown and described in U.S. patent application Ser. No. 08/926,380, entitled PATIENT-SUPPORT ASSEMBLY FOR THERMAL SUPPORT APPARATUS, the disclosure of which is hereby incorporated by reference. Other features of the patient support apparatus are discussed in detail in U.S. patent application Ser. No. 08/925,981, entitled CANOPY ADJUSTMENT MECHANISMS FOR THERMAL SUPPORT APPARATUS; U.S. patent application Ser. No. 08/925,873, entitled HINGED PANELS FOR A THERMAL SUPPORT APPARATUS; and U.S. patent application Ser. No. 08/926,383, entitled HUMIDIFIER FOR A THERMAL SUPPORT APPARATUS, each of which is also incorporated herein by reference.

The humidifier can be of conventional size and can be configured to be used in conjunction with any conventional patient support apparatus. During operation, fluid stored in the reservoir unit is transferred through an open valve to the vaporizer where a heating element changes the fluid into a vapor which is then delivered to the support apparatus. It is appreciated that the humidifier can be made from any conventional material or materials including, but not limited to, metal, plastic, foam, rubber, high temperature resistant materials and combinations thereof.

Figure 1:
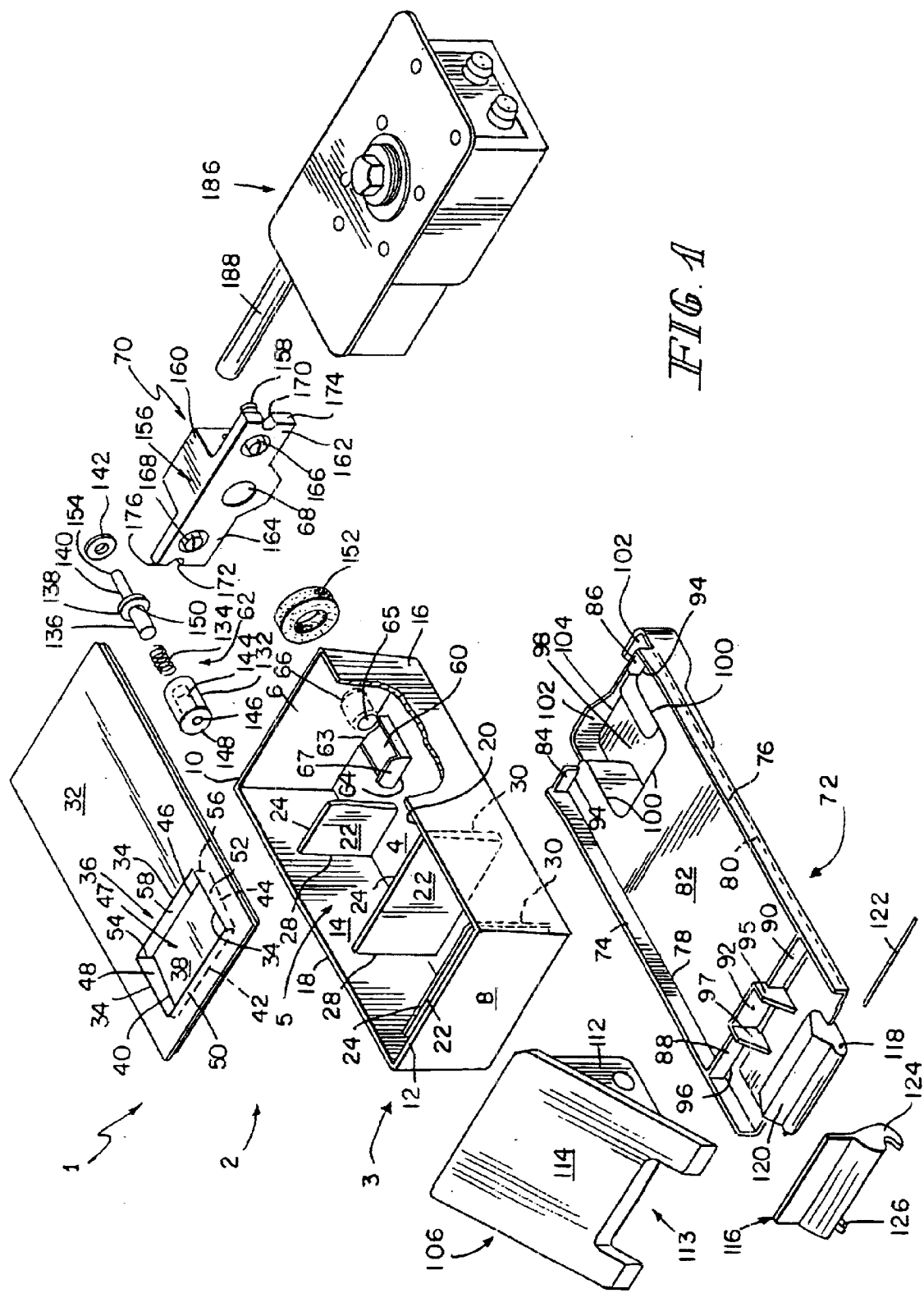
FIG. 1 is an exploded view of the humidifier according to one embodiment of the present invention.

Illustrative reservoir unit 2 includes a fluid storage container defining a reservoir 5 as shown, for example, in FIG. 1. Container 3 includes a bottom 4 and spaced apart first and second end walls 6, 8 attached to bottom 4 and extending upwardly therefrom. Each end wall 6, 8 includes a top edge 10, 12, respectively. In addition, container 3 includes spaced apart first and second side walls 14, 16 attached to bottom 4 and extending upwardly therefrom. Each side wall 14, 16 includes a top edge 18, 20, respectively. In the illustrated embodiment, top edges 10, 12, 18, 20 of end walls 6, 8 and side walls 14, 16 are generally coplanar. Additionally, side walls 14, 16 are attached to end walls 6, 8 and cooperate therewith so that container 3 is fluid impervious. Additionally in the illustrated embodiment, side walls 14, 16 and end walls 6, 8 are integrally appended to bottom 4 and container 3 can be molded from G.E.'s ULTEM®. It is within the scope of the invention, however, as presently perceived, to form container 3 using any suitable process and from any material that can provide a fluid impervious container and that can withstand a high temperature sterilization process.

Partitions 22 are appended to bottom 4 and extend upwardly therefrom as shown in FIG. 1. Each partition 22 is formed to include a top edge 24. Partitions 22 are configured to inhibit the flow of fluid within container 3 in order to minimize the amount of fluid that may splash when the caregiver is moving or refilling reservoir 5. Thus, it is within the scope of the invention as presently perceived to configure and arrange partitions 22 in any manner desired in order to achieve this result. Illustrative reservoir unit 2 includes three partitions 22 spaced apart between end walls 6, 8. Top edges 24 of partitions 22 are generally coplanar and are spaced apart beneath the plane defined by top edges 10, 12, 18, 20 of end walls 6, 8 and side walls 14, 16. However, it is within the scope of the invention as presently perceived to configure top edges 24 of partitions 22 to be generally coplanar with top edges 10, 12, 18, 20 of walls 6, 14, 8, 16 or even to extend top edges 24 of partitions 22 above the plane defined by edges 10, 12, 18, 20 of walls 6, 14, 8, 16 if space in patient support apparatus 26 so permits. To take advantage of the full storage volume of container 3, however, partitions 22 can be formed so that the fluid may flow between them. For example, partitions 22 may be formed to include openings therein (not shown). For another example, partitions 22 may be positioned so that there are openings between partitions 22 and one or both of side walls 14, 16 to provide a path for fluid communication between partitions 22.

Illustrative reservoir unit 2 is formed to include such openings even though top edges 24 are spaced apart from top edges 10, 12, 18, 20 of walls 6, 14, 8, 16 as shown in FIG. 1. Each partition 22 includes a first side edge 28 adjacent side wall 14 and a second side edge 30 adjacent side wall 16. However, each side edge 28 is spaced apart from wall 14 to form an opening therebetween and each side edge 30 is spaced apart from wall 16 to form an opening therebetween. Thus, it will be clear to those skilled in the art that fluid in any portion of container 3 may flow to any other portion of container 3 and that partitions 22 merely act to baffle the flow of fluid during movement of reservoir 5 to inhibit splashing.

Top edges 10, 12, 18, 20 of walls 6, 14, 8, 16 cooperate to define an opening in container 3 through which fluid may be added to reservoir 5 as shown in FIG. 1. A lid 32 is configured to cover the opening and is carried by top edges 10, 12, 18, 20 during use of support apparatus 26 when humidifier assembly 1 is not being cleaned or refilled. Lid 32 includes an edge 34 defining an opening 36 therethrough. A refill pan assembly 47, including a refill pan 38 having edges 40, 42, 44, 46 and three walls 48, 50, 52 appended to refill pan 38 and extending upwardly therefrom, is provided on lid 32. (See also FIGS. 4 and 5.) As can be seen, wall 48 is appended to edge 40 and extends upwardly therefrom, wall 50 is appended to edge 42 and extends upwardly therefrom, and wall 52 is appended to edge 44 and extends upwardly therefrom. Top edges of each of walls 48, 50, 52 of pan 38 are appended to edge 34 thereby mounting refill pan assembly 47 to lid 32 and leaving one portion of edge 34 undisturbed. Edge 46 of refill pan 38 cooperates with the undisturbed portion of edge 34 and with an edge 54 of wall 48 and an edge 56 of wall 52 to define an opening 58 that is in fluid communication with refill pan 38 and reservoir 5. Thus, it is appreciated that fluid can be deposited from a fluid source to refill pan 38 from which the fluid will flow through opening 58 into reservoir 5.

A channel 60 is formed on bottom 4 within reservoir 5 terminating at edges 63 and 64. Edge 63 is appended to wall 6. A channel stop 67 is appended to edge 64 opposite wall 6 and extends substantially upward from said edge. Channel 60 is configured to receive a portion of valve assembly 62. In the illustrated embodiment, an aperture 65 is disposed through wall 6. A valve guide 66 is provided adjacent wall 6 on the exterior of reservoir 5 and about aperture 65 to provide positional and directional support for valve assembly 62 to ensure proper connection with receptacle 68 in manifold 70. (See FIGS. 1 and 2.) Aperture 65 allows communication with the exterior of reservoir 5 to enable transfer of fluid to manifold 70.

In the illustrated embodiment, reservoir unit 2 is configured to couple to a slide 72. (See also FIGS. 2 and 4.) Slide 72 includes side rails 74, 76 which append to edges 78, 80, respectively of a basin 82, and extending upwards therefrom. End rails 84, 86 and 88, 90, 92 are appended to edges 94, 96, respectively, and are attached adjacent side rails 74, 76, respectively. Basin 82 is configured to receive reservoir unit 2 within rails 74, 76, 84, 86, 88, 90, 92 which cooperate to limit movement of unit 2 in the same plane as basin 82.

Figure 2:
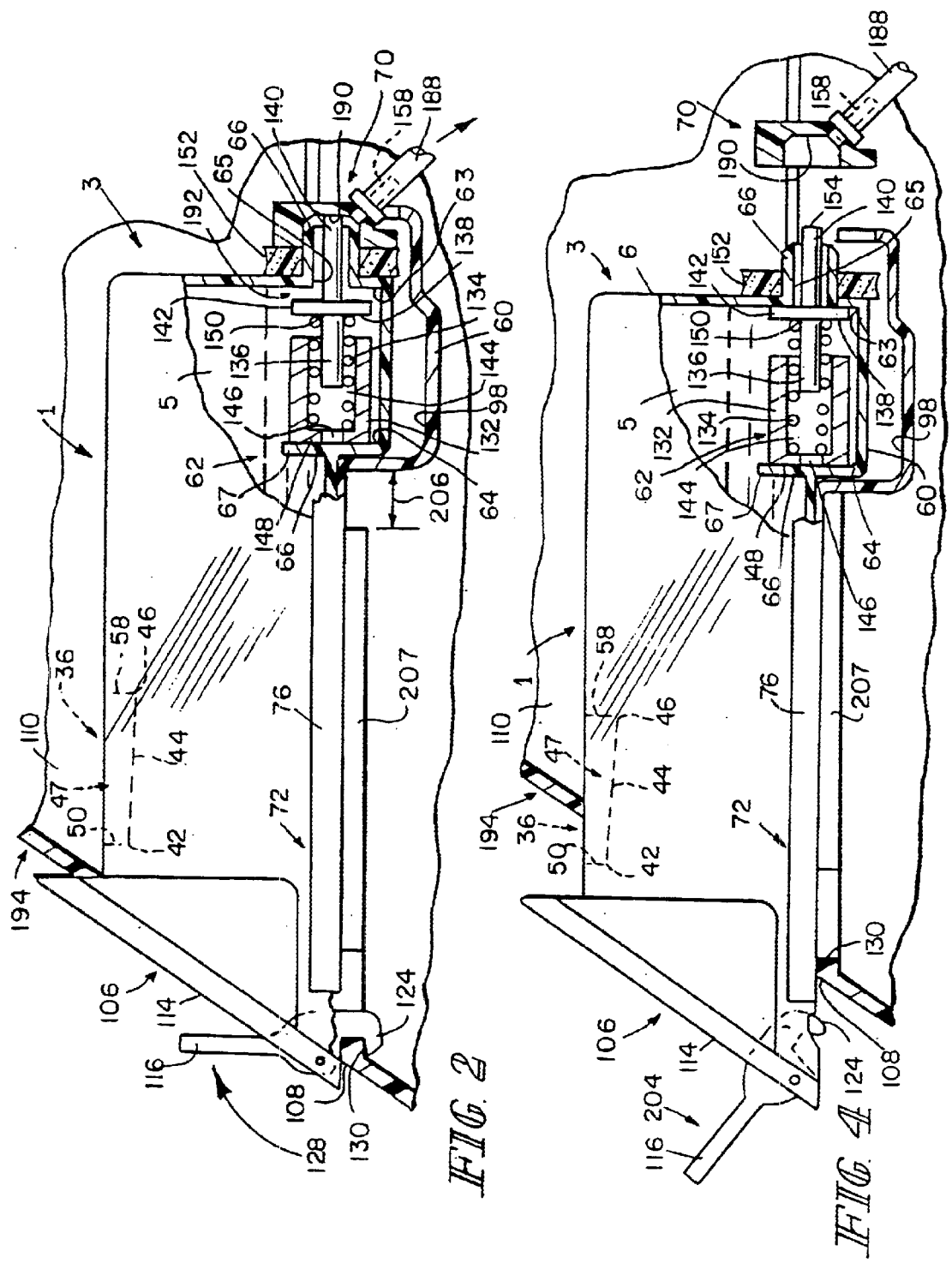
FIG. 2 is a sectional view of a portion of the patient support apparatus of FIG. 3, taken along line II—II.

Illustratively, braces 95, 97 are positioned adjacent rail 92 and basin 82 to assist in adding structural integrity to slide 72. Container 3 is configured to fit snug against rails 74, 76, 84, 86, 88, 90 and 92 ensuring a consistent positional alignment between valve guide 66 and receptacle 68 in manifold 70. Slide 72 further includes a catch basin 98 to collect any fluid that may escape reservoir 5, (e.g., at valve guide 66). Catch basin 98 is formed adjacent edge 100 of basin 82 and is positioned in an orientation under valve guide 66 when unit 2 is coupled with slide 72, as shown in FIGS. 2 and 4. A barrier 102 is appended to edge 104 of basin 98 and extends upward therefrom. The top edge of barrier 102 is appended to edge 100 thereby mounting basin 98 to slide 72.

Slide 72 still further provides a front panel assembly 106 configured to cover edge 108 of cavity 110. (Compare FIGS. 3 and 5.) In the illustrated embodiment, assembly 106 comprises a block portion 112 positioned adjacent wall 8 of container 3 and rails 88, 90, 92 of slide 72, opposite catch basin 98. Block 112 is configured to receive braces 95, 97. A front panel 114 is positioned adjacent block portion 112 opposite wall 8, as best shown in FIGS. 2 and 4. Front panel 114 is configured to serve as a covering for cavity 110. It is appreciated that block portion 112 may be attached to slide 72 by extending screws through basin 82 and into portion 112. It is further appreciated that front panel assembly 106 may be either attached to slide 72 or integrally formed therewith. In addition, front panel 114 may provide indicia on its surface to communicate information to the caregiver.

A handle 116 is hingedly attached to front panel assembly 106, as shown in FIGS. 1, 2 and 4. Handle 116 is a generally rectangular grippable body that the caregiver grasps to move reservoir unit 2. A bore 118 is disposed through a hub body 120 attached to basin 82 through which a pin 122 is extended. Hooks 124, 126 depend from handle 116 illustratively being spaced apart from each other on opposite sides of hub body 120, as best shown in FIG. 1. Handle 116 is configured to couple to pin 122 allowing said handle to pivot about bore 118. A recess portion 113 in front panel 114 is configured to receive handle 116. When handle 116 is pivoted in direction 128 to a generally vertical position, hooks 124, 126 are so configured to engage flange 130 on edge 108 thereby preventing movement of slide 72 in cavity 110. Conversely, when handle 116 is pivoted in direction 204 to a non-vertical position, hooks 124, 126 disengage flange 130 thereby allowing slide 72 to move within cavity 110.

Valve assembly 62 cooperates with reservoir unit 2 to selectively provide fluid communication between reservoir 5 and manifold 70, as previously discussed. (See FIGS. 2 and 4.) In the illustrated embodiment, valve assembly 62 comprises a stem valve block 132, a compressing spring 134, a stem 136, a seal base 138, a plunger 140 and a seal 142. Stem valve block 132 is a longitudinally extending cylindrical body having a hole 144 longitudinally disposed therethrough configured to receive spring 134. Stem valve block 132 is positioned in channel 60 between channel stop 67 and aperture 65 such that hole 144 is in substantial coaxial alignment with aperture 65. Spring 134 is positioned in hole 144 adjacent a flange 146 formed at end 148 of hole 144 which is positioned adjacent channel stop 67. Stem 136 is extended through spring 134 along its longitudinal axis, as best shown in FIGS. 2 and 4. Seal base 138 is coaxially attached to end 150 of stem 136. In the illustrated embodiment, plunger 140 is coaxially attached to seal base 138 projecting in a direction longitudinally opposite from stem 136. A seal 142 made illustratively from silicon, rubber or some other fluid impermeable material is provided adjacent seal base 138 and positioned opposite stem 136 and about plunger 140 (see FIGS. 2 and 4). Seal 142 is also positioned within reservoir 5 having a larger diameter than aperture 65 (see FIGS. 2 and 4). A seal 152 is fitted about valve guide 66 adjacent wall 6 between container 3 and manifold 70. Seal 152 prevents any substantial amount of fluid from leaking out of container 3. If, however, an insubstantial amount of fluid leaks from container 3, it will collect in catch basin 98.

Tip 154 of plunger 140 is extended through aperture 65 and through valve guide 66 being positioned to the exterior of reservoir unit 2. Valve assembly 62 is configured such that bias from spring 134 directs a force coaxial to stem 136 against seal base 138 forcing seal 142 against wall 6. This forms a generally water-tight seal around aperture 65 preventing fluid from escaping reservoir 5.

Figure 6:
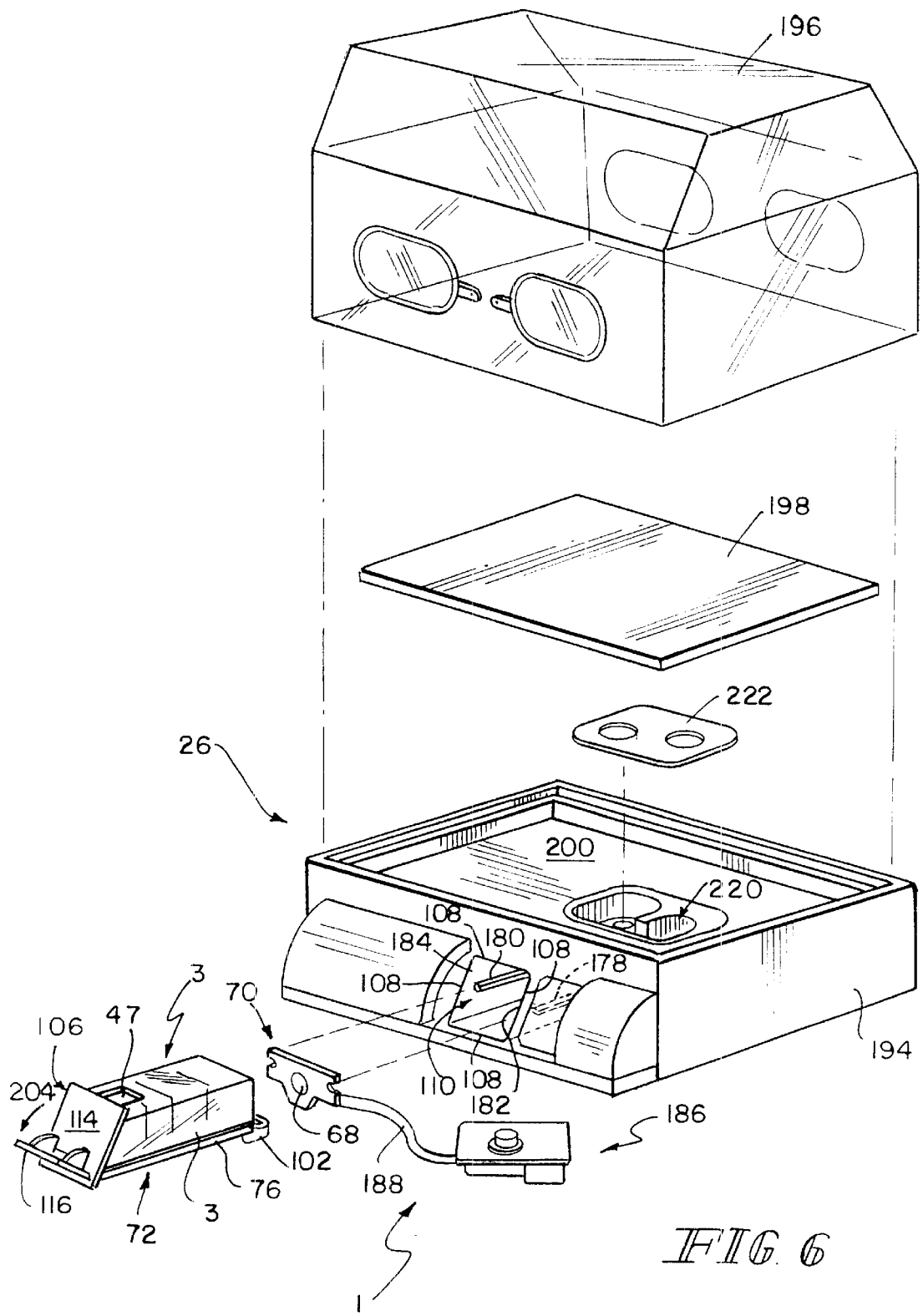
FIG. 6 is an exploded view of a portion of the humidifier and patient support apparatus according to one embodiment of the present invention.

Manifold 70, as shown in FIG. 1, comprises a T-shaped body 156 having a receptacle 68 and a coupling 158. T-shaped body 156 includes a central body 160 having laterally opposed flanges 162, 164 positioned at opposite ends thereof. Receptacle 68 is formed in body 160 and positioned between flanges 162, 164. Illustratively, receptacle 68 is a conically-shaped recessed portion of manifold 70, as best shown in FIGS. 2 and 4. Flanges 162, 164 include fasteners 166, 168 configured to attach to a support (not shown) within cavity 110 to maintain manifold 70 in a fixed position. It is appreciated that fasteners 166, 168 may be thumbscrews. Flanges 162, 164 also include rail guides 170, 172 formed at edges 174, 176. Rail guides 170, 172 are configured to engage rails 178, 180 longitudinally positioned along walls 182, 184 within cavity 110 as shown in FIG. 6. This ensures manifold 70 is correctly positioned if removed and replaced.

Manifold 70 is positioned within cavity 110 between reservoir unit 2 and vaporizer 186 as shown in FIG. 6. Coupling 158 is the conduit through which fluid exits manifold 70. Coupling 158 is in fluid communication with receptacle 68. A tube 188 is positioned in fluid communication with both coupling 158 and vaporizer 186 thereby allowing fluid to transfer from reservoir 5 into vaporizer 186.

As shown in FIGS. 2 through 5, slide 72 and reservoir unit 2 are configured to be movably fitted in concert within cavity 110 engaging and disengaging valve assembly 62. Reservoir unit 2 is movable between a first position having valve assembly 62 in an open position (see FIGS. 2 and 3), a second position that places valve assembly 62 in a closed position (see FIGS. 4 and 5), and a third spaced apart position (see FIG. 6).

Figure 3:
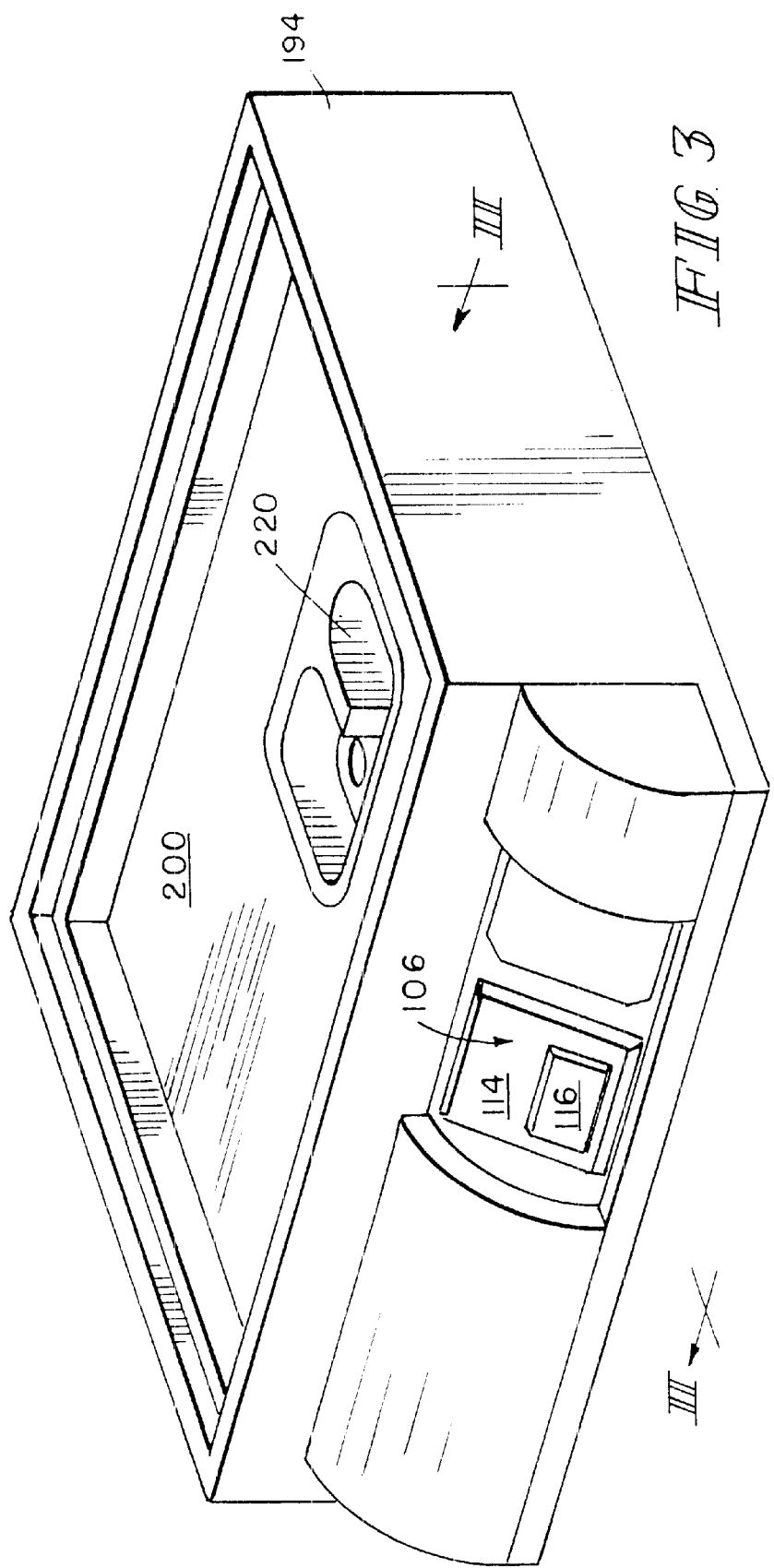
FIG. 3 is a perspective view of a portion of the patient support apparatus according to one embodiment of the present invention.

In FIGS. 2 and 3, slide 72 is shown in the first position allowing fluid communication between reservoir 5 and manifold 70. As shown in FIG. 2, slide 72 positions container 3 in cavity 110 such that tip 154 of plunger 140 engages back wall 190 in receptacle 68 of manifold 70. The interaction between plunger 140 and back wall 190 supplies sufficient reverse force against the bias of spring 134 causing plunger 140 to move seal 142 to a spaced apart position from aperture 65 allowing fluid to flow from reservoir 5 to receptacle 68 according to directional arrow 192 (i.e., the open position). As container 3 engages manifold 70, handle 116 is pivoted in direction 128 to cause hooks 124, 126 to engage ledge 130 in apparatus base 194, as shown in FIG. 2. The force exerted on ledge 130 by hooks 124, 126 maintains the reverse bias against seal 142 maintaining same in the open position.

Manifold 70 being in fluid communication with vaporizer unit 186, allows transfer of fluid from reservoir 5. Vaporizer unit 186 may be any conventional vaporizer that includes generally a float housing, a reservoir, and a vaporizer (all not shown). Illustratively, the float controls how much and when fluid will enter vaporizer unit 186. As fluid enters vaporizer 186, the reservoir becomes filled. Once the fluid reaches its full level, the float blocks tube 188. This prevents additional fluid from entering vaporizer 186. As fluid is being consumed by the vaporizer, the fluid level in the reservoir is reduced causing the float to open tube 188. Fluid is again allowed to enter the reservoir until the full level is reached. This process repeats until all the fluid from reservoir 5 is depleted. It is within the scope of the invention that the vaporization can be accomplished by any conventional method or device used for vaporizing fluids.

In FIGS. 4 and 5, slide 72 is shown in the second position such that reservoir unit 2 is in a spaced apart position from manifold 70 thereby preventing fluid communication between same. (i.e., the closed position.) When reservoir 5 is depleted of fluid, unit 2 can be moved to the second position to be refilled. To accomplish this, the caregiver grasps handle 116 and moves same in direction 204 to cause hooks 124, 126 to disengage from flange 130. Slide 72 is then free to move within cavity 110. The caregiver may, by grasping handle 116 again, move reservoir unit 2 a distance indicated by reference number 206 sufficient to expose opening 58 in lid 32. When reservoir 5 is moved to this partially spaced apart position, tip 154 of plunger 140 no longer engages manifold 70. Bias from spring 134 causes seal 142 to become repositioned adjacent aperture 65, preventing fluid from escaping reservoir 5. The caregiver may then pour fluid into the now exposed refill pan 38. Again, this can be accomplished without having to fully remove reservoir unit 2.

Reservoir unit 2 is also configured to be removable by the caregiver for cleaning purposes. Slide 72 is removable after hooks 124, 126 have been disengaged from flange 130 by lifting slide 72 and unit 2 in an upward direction thereby occupying the space provided in cavity 110. Basin 98 is lifted over base 207. Accordingly, unit 1 can be fully removed from cavity 110. For cleaning purposes, lid 32 is removable from container 3, whereas container 3 is removable from slide 72. In addition, valve assembly 62 is removable from channel 60 and assembly 106 is removable from slide 72. This allows all the components of humidifier unit 1 to be cleaned and sterilized individually.

Humidified air from vaporizer 186 enters the heater/impeller cavity 220 provided in base or tub 194 of the patient support apparatus 26. (See FIGS. 3, 5 and 6.) The heater/impeller cavity 220 heats and distributes the vaporized liquid from vaporizer 186. This humidified air is then circulated about patient support apparatus 26. A cover 222 is positioned over heater/impeller cavity 220, as shown in FIG. 6, to restrict the direction with which the vapor is fed into patient support apparatus 26. Patient support apparatus 26 also includes a deck 198, and a canopy 196. Deck 198 supports an infant and is placed on surface 200. Canopy 196 shrouds deck 198 creating an isolated environment for the infant. As the mist is released, it disperses throughout assembly 26 within canopy 196.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as set forth in the attached claims.

We claim:

1. A patient support apparatus comprising
a support having a container-receiving cavity;
a canopy situated above the support, the canopy cooperating with the support to provide a patient space; and
a humidifier operable to humidify the patient space, the humidifier comprising a vaporizer coupled to the support and spaced from the container-receiving cavity, a container for holding fluid and configured for insertion into the container-receiving cavity, and a valve assembly coupled to the container, the valve assembly having a movable portion that is movable relative to the container, the container being movable relative to the support between a first position in the container-receiving cavity and a second position in which the container is moved away from the first position but is still at least partially situated in the container-receiving cavity, the movable portion being in an opened position to permit fluid to flow from the container through the valve assembly and to the vaporizer when the container is in the first position, and the movable portion being in a closed position to prevent fluid from flowing out of the container through the valve assembly when the container is in the second position.

2. The patient support apparatus of claim 1, wherein the humidifier further comprises a slide mounted in the container-receiving cavity to support movement of the container between the first and second positions.

3. The patient support apparatus of claim 1, wherein the container is made from a material that can withstand high temperature sterilization.

4. The patient support apparatus of claim 1, wherein the container is movable to a third position outside the container-receiving cavity.

5. The patient support apparatus of claim 1, wherein the container further comprises a refill pan to which access is provided from outside the container-receiving cavity when the container is moved to the second position.

6. The patient support apparatus of claim 1, wherein the container includes a container wall, the movable portion includes a seal that engages the container wall when the movable portion is in the closed position, and the valve assembly further includes a spring that biases the movable portion toward the closed position.

7. The patient support apparatus of claim 6, wherein the humidifier further comprises a manifold mounted in the container-receiving cavity and in fluid communication with the vaporizer, and the manifold engages the movable portion to move the movable portion to the opened position when the container is inserted into the container-receiving cavity and moved to the first position to provide fluid communication between the container and the vaporizer.

8. The patient support apparatus of claim 2, wherein the slide further comprises a front panel positioned adjacent to the container and a grippable body to move the slide and the container between the first and second positions, and the front panel closes the container-receiving cavity when the container is inserted into the container-receiving cavity and moved to the first position.

9. The patient support apparatus of claim 2, wherein the slide includes a catch basin configured to be positioned under the valve assembly when the container is moved to the first position.

10. The patient support apparatus of claim 8, wherein the front panel further comprises a latch movable between a clasped position locking the container in the first position relative to the support and an unclasped position unlocking the container from the support.

11. The patient support apparatus of claim 7, wherein the movable portion further comprises a stem coupled to the seal and a plunger coupled to the seal, the spring is a coil spring that coils about the stem, and the manifold engages the plunger to move the movable portion from the closed position to the opened position against the bias of the spring when the container is moved to the first position.

12. The patient support apparatus of claim 11, wherein the container wall has an aperture, the seal and the stem are located inside the container, and the plunger extends from the seal through the aperture in the container wall.

13. The patient support apparatus of claim 12, wherein the stem and the plunger are aligned along a common axis.

14. The patient support apparatus of claim 1, wherein the container further comprises at least one partition provided therein to prevent fluid therein from splashing during movement of the container.

15. The patient support apparatus of claim 2, wherein the slide further comprises a catch basin positioned between the container and the vaporizer when the container is moved to the first position to catch leaked fluid between the container and the vaporizer.

16. An infant incubator comprising:

a tub carrying a patient support surface and including a container-receiving cavity; and a humidifier comprising:

a vaporizer coupled to the tub and spaced from the container-receiving cavity; a container for holding fluid and configured for insertion into the container-receiving cavity, and a valve assembly coupled to the container, the valve assembly having a movable portion that is movable relative to the container, the container being movable relative to the tub along a substantially straight path between a first position in the container-receiving cavity and a second position in which the container is moved away from the first position but is still at least partially situated in the container-receiving cavity, the movable portion being in an opened position to permit fluid to flow from the container through the valve assembly and to the vaporizer when the vaporizer is in the first position, and the movable portion being in a closed position to prevent fluid from flowing out of the container through the valve assembly when the container is in the second position, the movable portion moving parallel with the substantially straight path when moving between the opened position and the closed position.

17. An infant incubator comprising:

a tub carrying a patient support surface and having a wall defining a perimeter, the tub including a container-receiving cavity within the perimeter; and a humidifier comprising:

a vaporizer coupled to the tub, a container for holding fluid and configured for insertion into the container-receiving cavity, and a valve assembly coupled to the container, the valve assembly having a movable portion that is movable relative to the container, the container having a refill opening, the container being movable relative to the tub between a first position in the container-receiving cavity and a second position in which the container is moved away from the first position but is still at least partially situated in the container-receiving cavity, the refill opening being inside the perimeter of the tub and inaccessible when the container is in the first position, the refill opening being accessible outside the perimeter of the tub when the container is in the second position, movement of the container from the second position to the first position results in the movable portion moving from a closed position in which fluid is prevented from flowing out of the container through the valve assembly to an opened position in which fluid is permitted to flow out of the container through the valve assembly and to the vaporizer.

18. A patient support apparatus comprising:

a support having a container-receiving cavity, a vaporizer coupled to the patient support apparatus, a fluid supply container configured for insertion into and removal from the container-receiving cavity while the vaporizer remains coupled to the patient support apparatus, and a valve assembly coupled to the container, the valve assembly having a movable portion that is movable relative to the container, the container being movable relative to the patient support apparatus between a first position in which the container is received in the container-receiving cavity and a second position spaced from the first position, the movable portion being in an opened position to permit fluid to flow from the container through the valve assembly and to the vaporizer when the container is in the first position, and the movable portion being in a closed position to prevent fluid from flowing out of the container when the container is in the second position.

19. The patient support apparatus of claim 18, wherein the container moves along a straight path when moving between the first position and the second position and wherein the movable portion moves parallel with the straight path when moving between the opened position and the closed position.

20. The patient support apparatus of claim 18, wherein the container comprises a container wall that has an aperture and the movable portion includes a seal that engages the container wall to block the aperture when the valve member is in the closed position.

21. A patient support apparatus comprising:

a support having a container-receiving cavity, a vaporizer coupled to the support, a manifold mounted in the container-receiving cavity and in fluid communication with the vaporizer, a fluid supply container configured for insertion into and removal from the container-receiving cavity, the container having an outlet, and a valve assembly having a movable portion that is movable relative to the container between a closed position closing the outlet and an opened position opening the outlet, the movable portion moving from the closed position to the opened position in response to engaging the manifold during the insertion of the container into the container-receiving cavity to provide fluid communication between the container and the vaporizer through the outlet and the manifold.

22. The patient support apparatus of claim 21, wherein the movable portion comprises a plunger that extends through the outlet and that engages the manifold during the insertion of the container into the container-receiving cavity.

23. The patient support apparatus of claim 22, wherein the valve assembly includes a spring configured to bias the movable portion to the closed position when the container is moved away from the manifold to prevent fluid from flowing out of the container through the outlet.

* * * * *